(12) United States Patent
Gilad

(10) Patent No.: US 7,981,106 B2
(45) Date of Patent: Jul. 19, 2011

(54) ELECTRONICALLY-CONTROLLED DEVICE FOR RELEASE OF DRUGS, PROTEINS, AND OTHER ORGANIC OR INORGANIC CHEMICALS

(76) Inventor: Pinchas Gilad, Rehovot (IL)

( * ) Notice: Subject to any disclaimer, the term of this patent is extended or adjusted under 35 U.S.C. 154(b) by 0 days.

(21) Appl. No.: 12/392,105

(22) Filed: Feb. 25, 2009

(65) Prior Publication Data

US 2009/0216176 A1 Aug. 27, 2009

Related U.S. Application Data

(60) Provisional application No. 61/031,365, filed on Feb. 26, 2008.

(51) Int. Cl.
*A61K 9/22* (2006.01)

(52) U.S. Cl. .............. 604/890.1; 604/892.1; 604/501; 429/137

(58) Field of Classification Search ........... 604/890.1, 604/892.1, 20, 501; 429/137
See application file for complete search history.

(56) References Cited

U.S. PATENT DOCUMENTS

| | | | |
|---|---|---|---|
| 4,557,723 A | | 12/1985 | Sibalis |
| 4,639,244 A | * | 1/1987 | Rizk et al. ............... 604/19 |
| 4,731,049 A | | 3/1988 | Parsi |
| 4,734,090 A | | 3/1988 | Sibalis |
| 4,752,285 A | | 6/1988 | Petelenz et al. |
| 5,087,240 A | * | 2/1992 | Sibalis .................... 604/20 |
| 5,135,479 A | | 8/1992 | Sibalis et al. |
| 5,499,938 A | * | 3/1996 | Nakamoto et al. ........ 445/50 |
| 5,501,662 A | | 3/1996 | Hofmann |
| 6,041,252 A | | 3/2000 | Walker et al. |
| 6,123,861 A | | 9/2000 | Santini, Jr. et al. |
| 6,277,257 B1 | | 8/2001 | Paul et al. |
| 6,527,718 B1 | | 3/2003 | Connor et al. |
| 6,706,011 B1 | | 3/2004 | Murphy-Chutorian et al. |
| 6,808,522 B2 | | 10/2004 | Richards et al. |
| 6,890,583 B2 | | 5/2005 | Chudzik et al. |
| 6,896,659 B2 | | 5/2005 | Conston et al. |
| 6,979,351 B2 | | 12/2005 | Forsell et al. |
| 7,037,521 B2 | | 5/2006 | Mosack |
| 7,070,592 B2 | | 7/2006 | Santini, Jr. et al. |
| 7,081,189 B2 | | 7/2006 | Squires et al. |
| 7,108,680 B2 | | 9/2006 | Rohr et al. |
| 7,279,175 B2 | | 10/2007 | Chen et al. |
| 2003/0146757 A1 | * | 8/2003 | Aguero et al. ............ 324/453 |
| 2003/0176836 A1 | * | 9/2003 | Doukas et al. ........... 604/93.01 |

OTHER PUBLICATIONS

Ivor Brodie et al., "Vacuum Microelectronic Devices", Jul. 1994, IEEE, vol. 82, pp. 1006-1034.*
C. S. Ha and J.A. Gardella, Chem. Rev., 2005, 105, 4205-4232.
S.W. Song et al., Langmuir 2005, 21, 9568-9575.
J.S. Prescott et al., Nature Biotechnology 2006, 24, 437-438.
J.L. Viovy, Rev. Mod. Phys. 2000, 72, 813.
S. Kim et al., Chromatographia, 1995, 40, 345.
S.N. Krylov and N. Dovichi, Anal. Chem, 2000, 72, 111R-128R.

(Continued)

*Primary Examiner* — Kevin C Sirmons
*Assistant Examiner* — Edelmira Bosques
(74) *Attorney, Agent, or Firm* — Dekel Patent Ltd; David Klein

(57) ABSTRACT

A device for drug release including a drug reservoir including a gate, wherein opening of the gate releases a drug stored in the drug reservoir, an electronic command and control (C & C) unit in communication with the gate that produces a gate bias voltage and time profile supplied to the gate for controlling opening of the gate, and a power source for supplying power to the electronic command and control unit.

15 Claims, 5 Drawing Sheets

OTHER PUBLICATIONS

S. Cherkaoui et al., Chromatographia, 2000, 52, 403.

D.J. Harrison et al., Micro-machining miniaturized capillary electrophoresis-based chemical analysis system on a chip, Science, 1993, 261, 895-897.

L. Zhang et al,. Mmicrochip electrophoresis-based separation of DNA J. Pharm. Biomed. Anal., 2003, 30, 1645-1654.

H. Seiko et al., J. Vac. Sci. Tech., 2004, B22, 1353.

J. Kim et al. Electrophoresis 2002, 23, 782-793.

A. Abragam,The Principles of Nuclear Magnetism, Oxford University Press, 1961, p. 301-302.

C.A. Spindt et al., IEEE Trans. Elect. Devices, 1991, 38, 2355-2363.

Surface Chemistry of Biodegradable Polymers for Drug Delivery Systems, Chang-Sik Ha and Joseph A. Gardella, Jr., Chem. Rev. 2005, 105, pp. 4205-4232.

Functionalized SBA-15 Materials as Carriers for Controlled Drug Delivery: Influence of Surface Properties on Matrix-Drug Interactions, S.-W. Song, K. Hidajat, and S. Kawi, Langmuir 2005, 21, pp. 9568-9575.

Chronic, programmed polypeptide delivery from an implanted, multireservoir microchip device, James H Prescott et al., Nature Biotechnology vol. 24 No. 4 Apr. 2006, pp. 437-438.

Electrophoresis of DNA and other polyelectrolytes: Physical mechanisms, Jean-Louis Viovy, Reviews of Modern Physics, vol. 72, No. 3, Jul. 2000, pp. 813-872.

Fast Capillary-Scanning System for Detecting Fluorescently Labelled DNA Sequencing Fragments Separated by Capillary Gel Electrophoresis, S. Kim et al., Chromatographia vol. 40, No. 5/6, Mar. 1995, pp. 345-349.

Capillary Electrophoresis for the Analysis of Biopolymers, Sergey N. Krylov and Norman J. Dovichi, Analytical Chemistry, vol. 72, No. 12, Jun. 15, 2000, pp. 111R-128R.

Rapid Separation of Basic Drugs by Nonaqueous Capillary Electrophoresis, S. Cherkaoui et al., Chromatographia vol. 52, No. 7/8, Oct. 2000, pp. 403-407.

Microchip electrophoresis-based separation of DNA, Lihua Zhang et al., J. Pharm. Biomed. Anal. 30 (2003), pp. 1645-1654.

Novel Process for High-Density Buried Nanopyramid Array Fabrication by Means of Dopant Ion Implantation and Wet Etching, Meishoku Koh et al., Japanese Journal of Applied Physics vol. 40 (2001) pp. 2837-2839.

Electrophoretic mobility for peptides with post-translational modifications in capillary electrophoresis, Jeongkwon Kim, Electrophoresis 2002, 23, pp. 782-793.

Field-Emitter Arrays for Vacuum Microelectronics, C . A. Spindt, et al., IEEE Transactions on Electron Devices, vol. 38, No. 10. Oct. 1991, pp. 2355-2363.

* cited by examiner

ELECTRONICALLY-CONTROLLED DEVICE FOR RELEASE OF DRUGS, PROTEINS, AND OTHER ORGANIC OR INORGANIC CHEMICALS

CROSS-REFERENCE TO RELATED APPLICATIONS

This application claims priority under 35 USC §119 to U.S. Provisional Patent Application Ser. No. 61/031,365, filed Feb. 26, 2008, which are incorporated herein by reference.

FIELD OF THE INVENTION

The present invention generally relates to controlled-release of chemicals, therapeutic drugs, proteins and other organic or inorganic materials, and particularly to a device which is a universal platform having specific properties tailored to the specific application, such as in a Controlled Drug Release System (CDRS).

BACKGROUND OF THE INVENTION

In the prior art, most medications are administered by "classical", systemic methods. Common examples are oral intake, gastrointestinal discharge, inhalation, syringe injection to muscles or blood vessels and others. For treatments of a specific organ ailment, most of the drug material released by these "classical" methods is wasted. It is blocked, washed away and destroyed before reaching its designated target. In most cases, only an extremely small fraction of the administered medication finally reaches the desired destination.

These old fashioned methods are not just wasteful. Quite frequently, systemic drug administration entails harmful side-effect risks, e.g., damage to normally functioning organs, destructive interference with normal body functions, or drug addiction with severe long term dependence.

In response, the pharmaceutical industry is investing large resources, trying to develop new schemes of controlled drug release. These R & D efforts address the issues of targeting, timing and efficiency of pharmaceutics discharge. Implantable, controlled drug delivery units are extensively pursued as well.

Slow-release pharmaceutics capsules are widely used nowadays. A single intake is involved. Drug discharge is effective over lengthy periods, yet with ever diminishing diffusion rates. In most cases systemic drugs are involved, occasionally carrying risks of side effects. The scientific and technological issues associated with this type of drug administration are still under intense R & D efforts.

Recent efforts to develop slow-release, targeted, passive devices have met success, specifically with arterial stent implants. Thin coatings of special matrices storing bioactive agents found success in preventing restenosis or local infections. The storage capacity of the coating is very limited and operation time is restricted to 30-60 days. Yet, the therapeutic effectiveness, notwithstanding the minute doses of discharged drug, is impressive.

Another prominent technique, under considerable R & D efforts, uses various types of pumps, some without moving mechanical elements. External or implanted pumps are used for fluidic drug administration. Coupled to electronic units they offer good control of release rate and duration, spanning long operational periods. The drug reservoir of an implanted pump could be replenished periodically. However, drug discharge is systemic.

Pumps with no moving parts are also under intensive R & D efforts. Some pumps use electro-osmosis force to drive electrolytes in micron sized channels. In essence, the architecture is an adaptation of capillary electrophoresis devices.

Other novel ideas pertaining to drug release systems are widely pursued. One class relates to single-time operation capsules, with coupling to an external power source that radiates energy to the capsule cap. Absorbed energy brings cap rupture, followed by drug dispensation. The directed energy is in the form of ultrasonic waves or laser beams transferred by fiber optics to the capsule cap. Cap temperature rises due to the absorbed ultrasound or laser radiation, resulting in cap disintegration. Such capsules can be implanted at the most effective locations. With this scheme, timing and location are effectively controlled, but the dose rate and integrated dose are fixed a priori. Since drug release is indeed local, a small total dose is conceivable. Examples include ultrasonic driven capsules and laser activated units. Laser activated capsules need a fiber optic connection for laser-energy transfer to the device.

Other investigators suggest microchips for drug storage and local release on command. The microchips are typically processed by MEMS technology on silicon substrates. The microchips contain chemically etched micro-channels, where drugs, or drug combinations, are subsequently stored. Drug release is initiated by an electrical signal. In some models, a high current signal heats the microchip and either activates the drug itself or induces damage to the enclosure cap that opens a route to medication outflow. Various schemes of microchip activation are offered. In one version, molecules diffuse freely and release rate is controlled by selection of cap material. In another embodiment, the cap disintegrates on application of an electric current. Another option is electrochemical activation at the cap, followed by cap degradation. Yet another version offers electric-field activated ion-exchange, resulting in cap disintegration.

Laboratory size electrophoresis devices have been suggested for controlled drug delivery. The device is external to the patient body. Drug discharge is transdermal, thus sharing shortcomings inherent to "classical" delivery methods.

Another controlled drug administration method uses an electric field applied on blood vessels, enhancing either drug or gene penetration into blood cells (electroporation process). Electric fields of order 0.2-20 kV/cm drive the electroporation process. High voltage is required to produce effective electric-fields of this magnitude on a regular blood vessel. In line with this idea, release of tumor-killer agents, encapsulated in non-permeable liposome, has been suggested. Strong electric-fields will force electroporation, delivering the toxic agent at a specific location, hence bypassing full body exposure.

Electrophoresis devices have become the universal tool for separation and identification of large organic molecules. The most common application at present is DNA separation and genome mapping. Separation is based on mobility variation between charged molecules subjected to an applied electric field. Electric fields in the order of 50V/cm are typical to this method. Since, in most cases, the length of the electrophoresis device is measured in tens of centimeters, the applied voltage is in the order of kilovolts.

The electrophoresis device is loaded with gel material. The gel forms narrow, twisting pores confining the molecular motion. Surface effects from gel walls are extremely important in determining the molecular flow. Effective charge state and drag forces are controlled by gel surface effects. The molecular drift path is contorted, becoming significantly extended relative to the instrument length. Molecular drift is slowed down considerably. Molecular-mass differentiation is obtained effectively over large distances and the process is time consuming.

In recent years, miniaturization of the laboratory size electrophoresis devices has taken place at an accelerated pace. Capillary electrophoresis systems are the result of these efforts. Narrow mechanical capillary channels, sized similar to gel pores, are the retarding medium.

The capillary electrophoresis devices have the benefits of lower bias voltages, increased molecular velocities, and short separation times. Electric fields of over 200V/cm are common, inducing faster molecular drifts. The miniaturization efforts had an impressive impact on the race to genome mapping, resulting in genome mapping periods much shorter than originally envisioned.

Electrophoresis devices were harnessed to drug delivery during the last 15 years. Laboratory size devices were suggested with transdermal administration. However, the method did not receive much demand. The presence of a high voltage bias is not entirely friendly to the human environment.

As regards size, even capillary electrophoresis systems are too big to serve as implanted drug delivery units. Indeed, the capillaries are small in diameter, in the order of 50 micrometers, but their length varies from 50-500 millimeters.

SUMMARY OF THE INVENTION

The present invention seeks to provide a device for electronically controlled-release of chemicals, therapeutic drugs and other organic or inorganic materials. The controlled drug release system (CDRS) is implanted in the patient's body, at the organ solely associated with the ailment. It is anchored at the location of maximum therapeutic effectiveness. Local drug administration guarantees maximum effectiveness, notwithstanding the minute doses of administered drugs. Internal or external release-commands are optional. Medications can be administered in a continuous or intermittent fashion, conforming to the best medical procedure. Dose rates are adjusted to the local levels deduced from present pharmaceutical practice.

Throughout the specification and claims, the term "drug" encompasses any kind of medicinal substance, as well as proteins, and other organic or inorganic chemicals.

The device includes a storage volume, an active gate, a power source and an electronic unit. The innovative miniature gate controls the open/close state and release rate from the apparatus. The integrated device can be miniaturized to a millimeter cube. No constraints are anticipated for increased volumes. In all cases, most of the volume is dedicated to the storage subunit. Release rate can be controlled over many orders of magnitude. Time release profile is adjustable according to an optimal specified routine. Using the same design principle, a multitude of applications is envisioned. In essence, the device is a universal platform having properties directly tailored to the selected application.

The most demanding application is an implantable CDRS. The CDRS is to be anchored at a specifically designated organ tissue for effective medical treatment. A large variety of ailments can be treated by this technique.

A gate coupled to a container and to a power source controls drug administration. Submicron gate-openings and nanometer scale electrode protrusion-tips are typical gate-design parameters. The release is under active control. It is adjustable over orders of magnitude in dose rates and/or total dose. High drug efficiency is obtained since medications are directly discharged at the targeted locations. Side effects are eliminated; only minute drug quantities are required locally. Drug secretion can be continuous or intermittent. Under intermittent administration, a practically unlimited number of release cycles are envisioned. Extended operational lifetime of the CDRS is projected. A high degree of reliability characterizes the design and operation.

Apart from drug release, a multitude of applications is projected. One example is controlled release of catalysts targeted for regulating chemical reactions. Another use is found in medical screening. The field of molecular biology can benefit from various models of the device. Remote sensing or tracing materials are potential applications as well.

The invention thus comprises a versatile drug delivery platform, based on a novel gate design, having one or more of the following properties:

1. Drug release on command: gate open/close. Multi-cycle operation.
2. A large spectrum of drugs or drug combinations is feasible.
3. Exceedingly accurate dose rates.
4. Local drug release of minute dose-rates and total dose rations, which eliminate systemic side-effects
5. Drug selection, release rate and dose figures easily tailored to established medical routines.
6. Continuous or intermittent release modes according to optimal medical procedure.
7. Large number of operational cycles: no gate limitations.
8. Advanced gate design eliminates external material penetration into the device.
9. Universal design platform: details easily tuned to specific drug properties and medical protocol.
10. Dimensions and shape fashioned in accordance to available space at the specific targeted site.
11. Manufacturing done using well-established processes using biocompatible materials. Flexible manufacturing procedures easily tailored to specific drug attributes.
12. Long operational life of implanted device
13. Inherent reliability based on modular construction and critical-element redundancy.

There is thus provided in accordance with an embodiment of the invention a device for drug release including a drug reservoir including a gate, wherein opening of the gate releases a drug stored in the drug reservoir, an electronic command and control (C & C) unit in communication with the gate and including an external C & C unit and an internal C & C unit that produces a gate voltage as controlled by the external C & C unit, the internal C & C unit controlling gate bias voltage and time profile supplied to the gate for controlling opening of the gate, and a power source for supplying power to the electronic command and control unit.

In accordance with an embodiment of the invention the gate includes an external electrode formed with at least one exit pore, an internal electrode, an insulating layer that insulates between the external and internal electrodes, and a field enhancing member that extends into the at least one exit pore. The field enhancing member may be a rod or cone.

In accordance with an embodiment of the invention the gate further includes an additional electrode located between the external and internal electrodes, and insulated from the external and internal electrodes by insulating layers.

In accordance with an embodiment of the invention the internal C & C unit includes a charging element for the power-source and a communication circuit tuned to the external C & C unit.

In accordance with an embodiment of the invention the external C & C unit is programmable to provide a delivery routine in accordance with an individual patient response.

In accordance with an embodiment of the invention the gate operates as a reversible pump, wherein a first polarity of the gate bias voltage causes ejection of molecules from the drug reservoir, and a second polarity of the gate bias voltage causes molecules external to the drug reservoir to be sucked into the drug reservoir.

In accordance with an embodiment of the invention the gate bias voltage suppresses molecular flow of fluids into the device.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

More Detailed Description of Drawings

Figure 1:
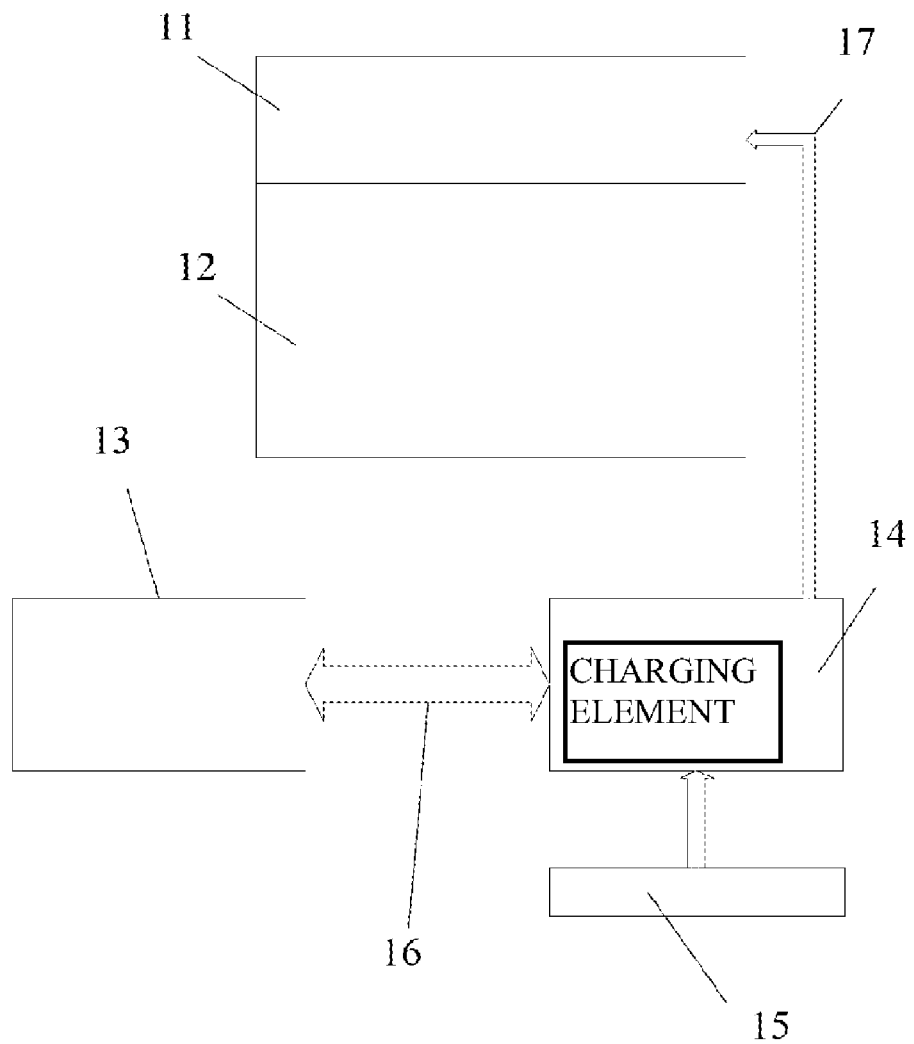
FIG. 1. Block diagram of an integrated drug release device.

FIG. 1 presents a block diagram of an integrated drug release device. The gate 11 is combined with the drug reservoir 12. The electronic command and control C&C block is divided into two separate units. The external electronic unit 13 holds the major part of the hardware and software. It could even be programmable along with individual-patient response to the delivery routine. The internal C&C unit 14 is functionally much simpler. It produces the gate voltage as dictated by the external unit. It controls bias-voltage and time profile supplied to the gate. The appropriate gate bias is transferred to the gate through a wire link 17 (or could be wireless). In addition, the internal C&C unit 14 contains a charging element for the power-source, and a communication circuit, tuned to the main, external C&C unit 13. The wireless communication link 16 can be rudimentary, of low transfer rate and limited vocabulary.

The power source 15 supplies the voltage for all needs of the internal electronic circuitry and gate bias.

Figure 2A:
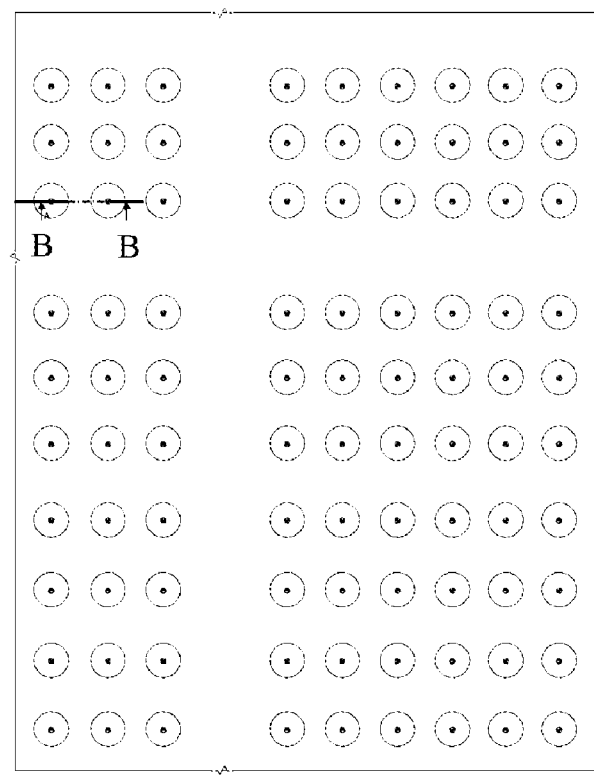
FIGS. 2A-2B. Schematic drawing of a two-electrode gate structure.
Figure 2B:
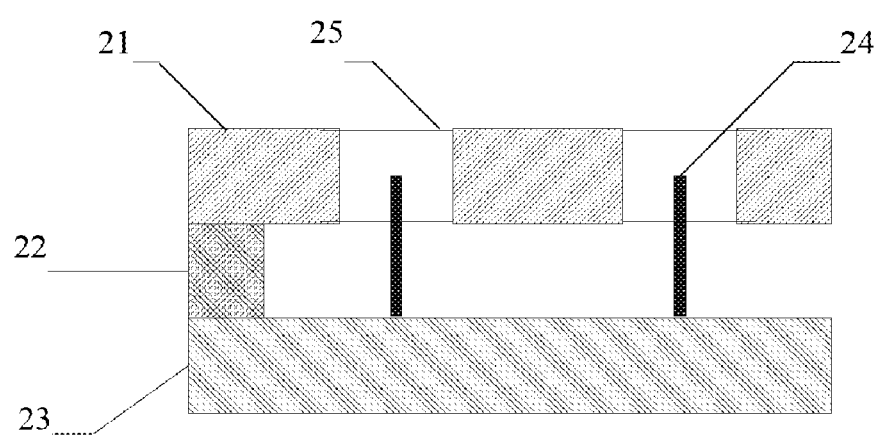

FIGS. 2A-2B are schematic drawings of a two-electrode gate structure. Note that the drawings are not to scale. Exit-pore diameter typically varies between 200 nm and 5 micrometers. Insulator thickness is typically 2-10 micrometers. Pitch distance is typically 5-100 micrometers. In FIGS. 2A and 2B, the field-enhancing elements are high aspect ratio rods. FIG. 2A is a top view of the gate structure with a matrix of pores. FIG. 2B shows a section through the various layers with the following components: the external electrode 21 with its exit-pores 25, thick insulating layer 22, internal electrode 23 and field enhancing rods 24.

Figure 3:
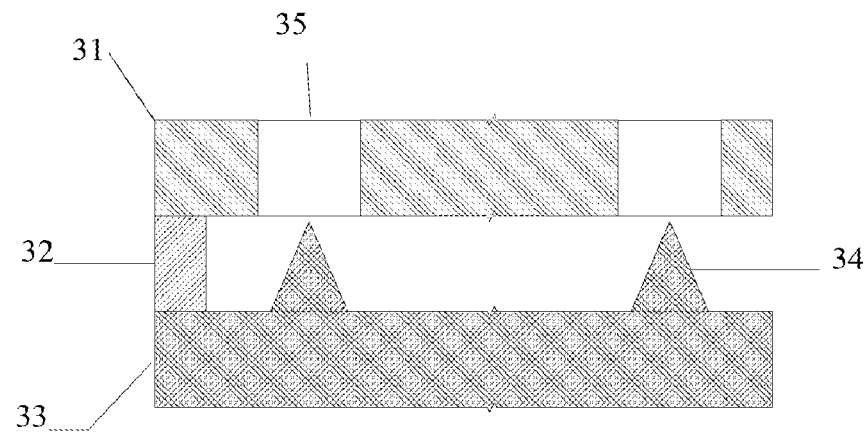
FIG. 3. View of pore-cone cells.

FIG. 3 is a view of two exit cells (not to scale). The field enhancing rods are replaced by cones 34. The cone angle and height are controlled by the parameters of the growth routine, as for example in the Spindt growth method (C. A. Spindt et al., IEEE Trans. Elect. Devices, 1991, 38, 2355-2363, the disclosure of which is incorporated herein by reference).

Figure 4:
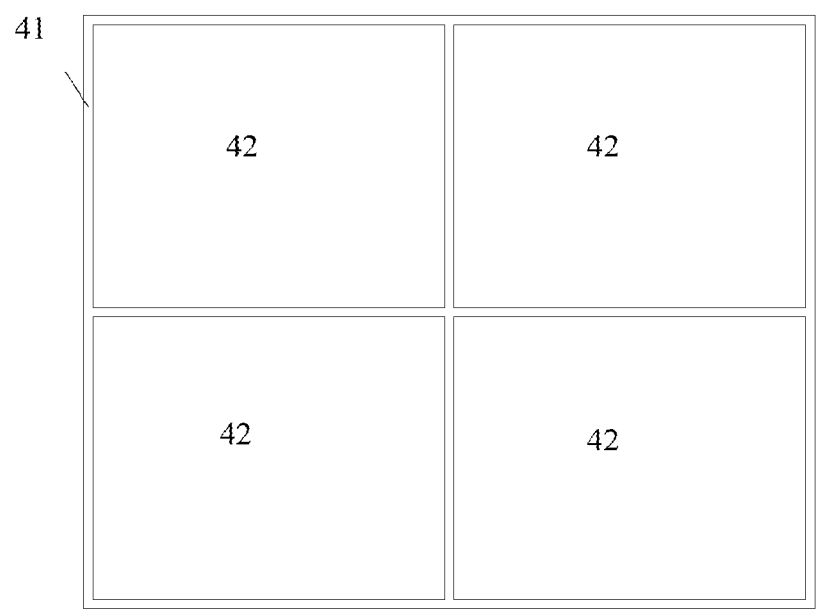
FIG. 4. A modular type gate with four independent subunits.

FIG. 4 presents a modular type gate with four independent subunits 42. The subunits are electrically insulated from each other by surrounding insulating strips 41. Each subunit is wired independently to the internal C & C unit. Parallel operation of subunits will considerably enhance device reliability.

Figure 5:
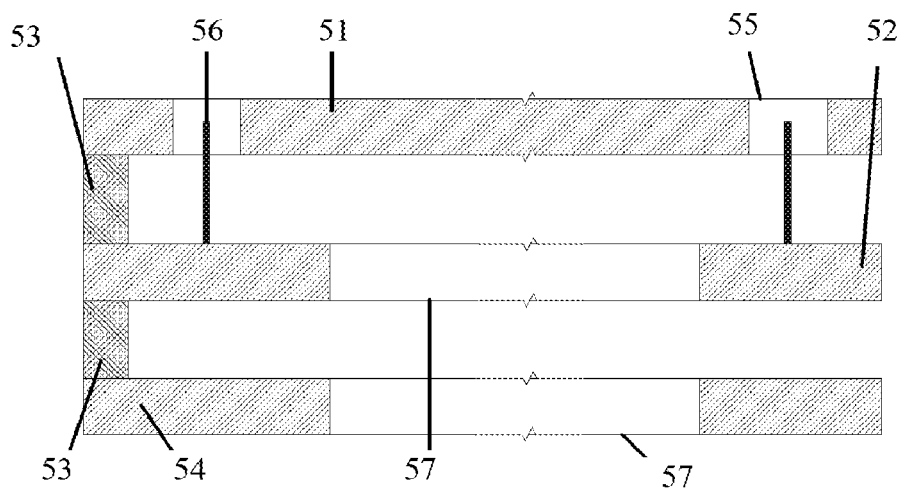
FIG. 5. Schematic drawing of a three-electrode gate structure.

FIG. 5 is a schematic drawing of a three-electrode gate structure. Dimensions are not to scale. The figure shows a section through all gate layers with the following elements: the external electrode 51 with exit-pores 55, the intermediate electrode 52, the innermost electrode 54, two thick insulating layers 53, the field enhancing rods 56 and feed holes 57. Feed holes diameters are much larger than exit-pore diameters. Typical dimensions of feed holes are 10-50 microns.

Figure 6:
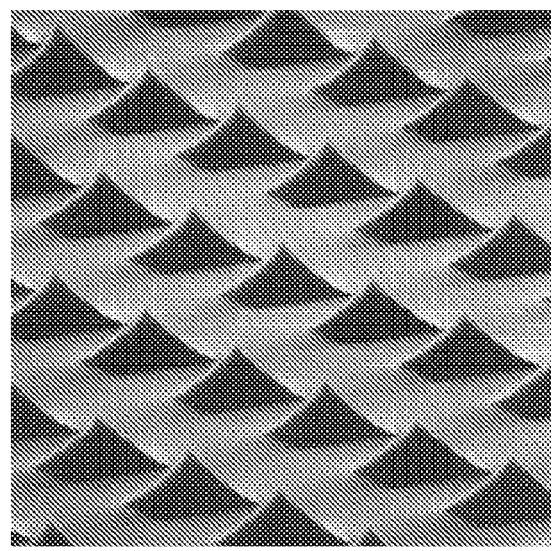
FIG. 6. Electron microscope photo of a pyramid array.

FIG. 6 brings a scanning electron microscope photo of a pyramid array. Note the regularity and uniformity of the pyramids. These qualities are within standard results of MEMS production methods. The matrix pitch is controlled by the lithographic mask. Pyramid parameters are determined by the MEMS process and are accurately controlled.

Figure 7A:
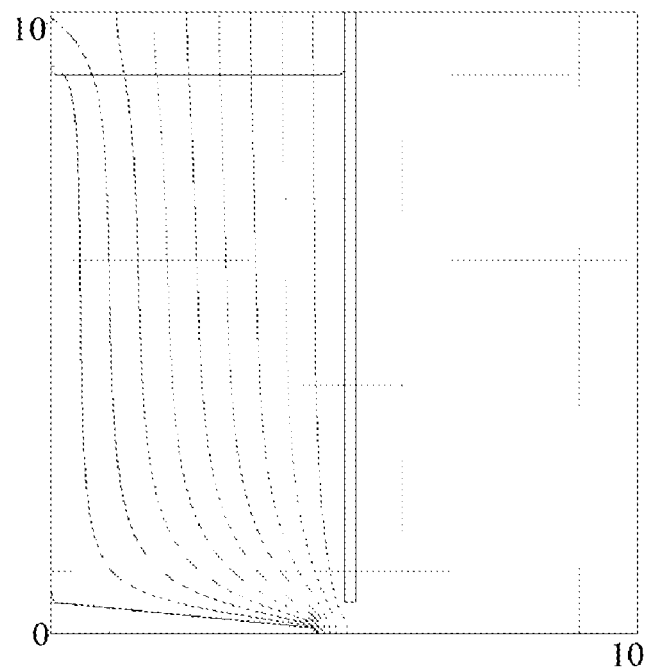
FIGS. 7A-7B. Calculation results of the electric potential and the electric field distribution in a single matrix cell.
Figure 7B:
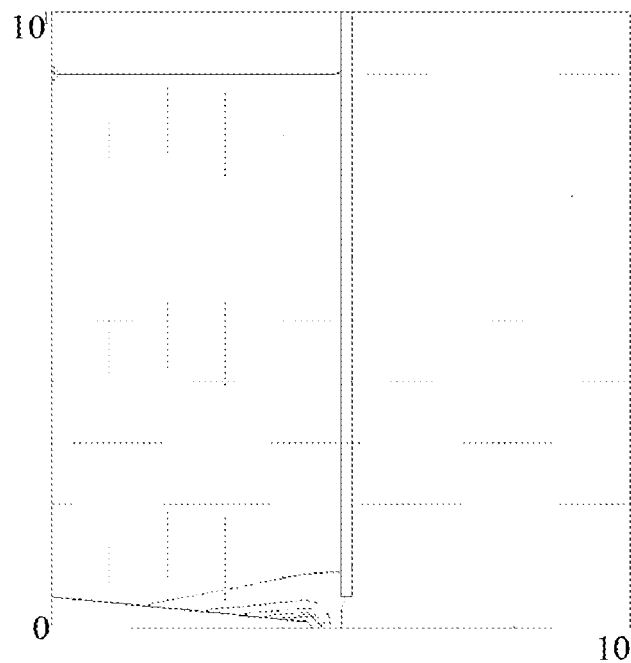

FIGS. 7A-7B displays calculation results for electric potential and electric field distributions in a single matrix cell. Axial symmetry is assumed in this modeling. In the figures, the Z axis is the symmetry axis. The figures show one-half of the planar section through the axis. With no loss in generality, we use in the calculations arbitrary values for cell dimensions and bias voltage. In the modeling, the gap between the external and internal electrodes is 5 micrometer. The exit pore diameter is 1 micrometer. The height of the field enhancing cone is 4.5 micrometers. The matrix pitch is 20 micrometers. The calculation is done for a cylinder of 10 micrometer length and 10 micrometer radius. The outer electrode is at ground potential and the inner electrode is biased at 20 mV. A dielectric constant k=1 is assumed.

FIG. 7A presents the potential distribution in the cell. The equipotential lines are drawn at 2 mV intervals. Inside the cell and away from the pore opening, the equipotential lines are parallel to the electrodes, producing a quasi constant electric field with the average value, e.g. the bias voltage divided by the electrode-gap. At the exit region the equipotential lines curve and pack around the cone tip. Electric field enhancement is thus produced. The external electrode and the pore opening at the exit plane are at the same, ground, potential. No equipotential lines extend outside the gate, to the enclosing tissue.

FIG. 7B shows the electric field distribution in the cell. Equal electric-field lines are depicted. For simplicity we limit the displayed electric-field values to the range of 200-600 V/cm. Line separation is 100 V/cm. All field values in this range are obtained in the tip/pore vicinity. The field between the electrodes, away from the exit pore, is an order of magnitude lower, within 35-40 V/cm. At the external pore opening plane the electric field drops to zero.

It is noted that all the dimensions and values herein are exemplary and non-limiting to the invention.

More Detailed Description of Embodiments

In accordance with an embodiment of the invention, the device includes an electrically controlled gate, a drug reservoir, a power source with optional recharging circuit and an electronic unit, including command and control circuitry.

A block diagram of an integrated drug release device, with the above elements, is presented in FIG. 1. The basic gate design comprises a two-electrode structure. A matrix of protrusions is grown on one electrode, facing holes drilled into the second electrode. Several protrusion geometries are possible. They can take the form of pyramids or cones. These pyramids or cones have sharp tips of order 10-100 nanometers in diameter. High aspect-ratio (length to diameter ratio) metallic or carbon nanorods, of order 10-100 nanometers in diameter, can replace the pyramids or conical structures. A combination of these structures, like high aspect ratio rods on pyramid bases is also possible.

The two electrodes are separated by an insulating layer, which mechanically supports the structure. Separation gap between electrodes is typically a few micrometers. The pyramids, cones or nanorods are also typically of order micrometer in height. The opposing pore to each pyramid, nanorod or cone has a typical diameter in the order of 200-5000 nm. Separation between pores in the array (matrix pitch-distance) in a typical application is 5-10 micrometer. The overall gate length and width are tuned to specific dose and rate considerations. They can vary between millimeters to centimeters. The gate shape is not necessarily a square. It can be freely designed to fit the geometrical features of the target organ.

The volume between the two electrodes is filled with the ionic drug molecules. Voltage applied between the two gate electrodes will induce an electrophoresis process. It will force an oriented molecular-drift out through the small pores in the external electrode. The nano scale dimensions of the tips produce high electric fields even at very low bias voltages. Transit times of the molecules will be very short due to the small drift distance in the gate. Flow rates can be adjusted in relation to applied voltage, pulse-duration and gate dimensions.

A more complex gate structure will include three electrodes, biased such that the gate region is slightly over-pressured during idle periods. During such idle periods the external electrode is oppositely biased, eliminating drug spill off, notwithstanding the slight over-pressure maintained at the gate region. This three-electrode structure will also inhibit diffusion from the environment into the drug delivery system.

The drug reservoir is an impermeable container made of elastic material. It will collapse when drug release is taking place, hence eliminating voids and vacuum formation. Size and shape are pre-designed to accommodate the device in the available targeted space.

The power source is a miniature rechargeable battery or capacitor of small dimensions. Inductive wireless recharging of an embedded battery or a storage capacitor is part of the design. Electronics and control/command units can be integrated as well. These sub-units are not vital in simple continuous operation modes. Yet they can be easily incorporated in advanced models.

One part of the invention is the gate structure. FIGS. 2A-2B show schematically a two-electrode gate structure. The gate comprises two parallel electrodes. Both electrodes are electrically conductive. Good electrical conductivity of the electrodes is not critical. The electrode surfaces are coated with thin films of insulating material. A thick, hollow layer of insulating material separates the two electrodes. The thick insulating layer fully extends all along the electrode rim. It supports the gate structure mechanically. The insulating layer and the two electrodes are bonded together, forming a tight enclosure, impermeable to body fluids. Most of the volume between the two conductive electrodes is hollowed. This volume will be filled by drug load.

Insulating strength allows biasing of over 100V between the conductive electrodes, with no risk of voltage breakdown. Yet typical operating voltage is less than 1V. The electrodes can be either metal or doped Silicon. The insulating layer and coatings can be $SiO_2$ or polymer material. All construction materials are human body compatible and meet health management guidelines.

The gate is a sealed structure except for pores drilled or otherwise formed into the two electrodes. A small number of drug feed-holes are produced in the inner electrode, whereas a large number of exit-pores are drilled in the external electrode. In effect, the external electrode is perforated by a matrix of pores. Centered against every external electrode pore we produce a bulging tipped structure, grown on the inner electrode. The tipped structures can be of cylindrical, conical, pyramidal or any other shape or combinations. These protrusions typically terminate with sharp tips. The pyramids or cones have typically tips of order 10-100 nanometers in diameter. In another embodiment, metallic or carbon nano rods, typically 10-100 nanometers in diameter, replace the pyramids or conical structures.

Pore diameter is chosen in tune with drug characteristics: molecular radius, ionic charge, mass and mobility. Typical pore diameter is from 200 nm to a few micrometers. The distance between pores (matrix pitch length) corresponds to medication attributes: prescribed rates of release, release time-sequence and total dose. Typical pitch length is 5-100 micrometers. It can vary over a larger range. Typical dimensions of the protrusions are: height 1-5 micrometers, base width (diameter) 1-5 micrometers, tip diameter 10-100 nm. The protrusions can be mounted on pedestals with height in conformity with insulator thickness. Electrode insulating coatings are typically of order 10-100 nm. The insulating layer is typically 2-10 micrometers thick, yet can reach 100 microns. The above are typical dimensions. Actual size is tailored to the specific medication characteristics.

FIG. 3 shows schematically an enlarged view of pore-cone cells. The design is basically modular. The gate can be split into subunits, located side by side on the container walls. Every subunit is electrically insulated from the others. Thus, each subunit can be independently biased. This feature gives another operational freedom: parallel operation of selected subunits or an independent operation of any single unit. Such a design will further increase pharmaceutical discharge control. This feature has important implications as regards device reliability, to be discussed later. FIG. 4 shows a modular type gate having four independent subunits.

A more complex gate structure will include three electrodes. FIG. 5 presents schematically the three electrode version. The third, innermost, electrode is positioned below the intermediate one, with the conical or pyramidal matrix. It is also conductive and coated with a thin insulating material. A thick insulating layer separates the third and second electrodes and serves as a support. The third electrode will have holes oriented against the feed holes in the intermediate electrode. Separation distance between the intermediate and innermost electrodes is typically 2-5 micrometers. The inner electrode is hermetically sealed to the container wall. Drug supply to the gate structure is through the feed holes.

The three electrode structure adds a large measure of reliability to the device. By controlling the voltage values and polarities we eliminate drug spill-offs or diffusion of external molecules into the device during idle periods.

Gate unit manufacturing is within routine procedures of present MEMS technology. Forming pyramids structures on Silicon substrate is a well-known technique, resulting from non-isotropic chemical etching. Selecting the appropriate Silicon axial orientation and using routine FAB processes, i.e. optical lithography, thin layer coatings and etching procedures will produce pyramidal structures. Etching duration is another factor controlling the end-result. The technique is currently used in mass produced Silicon pyramids, utilized in field emission displays. An example of a detailed procedure for silicon pyramids production is described in H. Seiko et al., J. Vac. Sci. Tech., 2004, B22, 1353, the disclosure of which is incorporated herein by reference.

FIG. 6 presents a Scanning Electron Microscope (SEM) photo of a pyramid array. Geometrical tolerances for pyramid dimensions, pitch distance and orientations are typically controlled to levels much superior to the demands of the CDRS gate element.

The pore-matrix in the external or the inner electrodes are also processed with well-established methods, comprising optical lithography, thin layer coatings and chemical etching. The process is employed for many years in MEMS technology. Accuracies and dimensional tolerances exacted in the MEMS industry are beyond the gate structure specifications. Alignment of the pyramids against the opposite pores and bonding together gate-elements can be done with old fashioned MEMS tools, used in integrated circuit (IC) industry for over 20 years.

When voltage is applied between the electrodes, the tipped protrusions in each matrix cell enhance the electric field at the pore region. Typical electric fields used in laboratory electrophoresis devices are of order 50V/cm. Capillary electrophoresis systems use higher electric fields, 100-200 V/cm. The increased electric-fields induce higher molecular drift velocities. In principle we can apply electric field far greater than currently used in capillary electrophoresis devices, increasing substantially the molecular drift velocity and release rate. Due to the short traveling distance out of the gate, this can be done without the risk of unfolding the drug molecules.

FIGS. 7A-7B present calculation results showing the electric field distribution in a single CDRS matrix cell. The electric fields are due to a biasing voltage of only 20 millivolts. In this model-calculation the cone height is 4.5 micrometer, the pore diameter is 1 micrometer and the insulator is 5 micrometers thick. Eventually, enhanced electric fields are produced around the cone even at the low applied voltage. Reducing the pore diameter will further increase the electric field. The combination of high electric fields and short drift distances will result in rapid discharge of drug molecules.

Note in FIG. 7 that the extension of the electric-field outside the gate-structure is minimal. It is confined to a very small region and has a very small value relative to field value inside the cell. Consequently, the CDRS environment, even at close proximity to the gate, will not be influenced electrically by the presence of the inter-gate fields. We should stress the importance of this property, since unlike other proposed systems using electric fields, the CDRS presented here is not susceptible to electric field cancellation by tissue fluids.

The protrusions facing the pores in the external electrode, in addition to their field enhancement role, supply the surface effects that are essential to the electrophoresis drift. In many cases, the insulation layer on the protrusions is also crucial for driving the electrophoresis motion through the creation of a double layer polarization.

The voltage polarity is dictated by the drug attributes. Voltage profile is related to the drug properties, drug-carrier characteristics and the selected medical routine. Voltage format can be either DC, alternating or pulsed. Both polarities can be applies in intervals of the selected time profile. These voltage parameters are adjusted at will by the control electronics. During drug release the polarity is switched to out-flow condition. During gate idle-periods we can eliminate drug flow by a small inverse polarity on the gate. A low-level inverse electric field can be applied continuously. The inverse bias is a gate-keeper. On command, the voltage will change polarity and field value set according to release protocol.

A small overpressure inside the gate region is also optional. During idle periods overpressure will inhibit molecular exchange through diffusion of tissue molecules. Conceivably, over-pressure of gate-region will result automatically with container collapse as drug flows out. As an alternative, over-pressure is attained in the three-electrode structure by proper gate-electrodes bias. A small forward field between the intermediate and internal electrodes will push drug molecules into the gate unit and exclude voids in the inter-electrode region.

We can make a conservative estimate of drug flow rates, based on data extracted from mobility studies performed with capillary electrophoresis devices. We use experimental parameters together with mobility analysis results, performed over a large spectrum of peptide molecules, listed in J. Kim et al. Electrophoresis 2002, 23, 782-793. The results cover a mass range of 150-2200 Daltons and charge range of 0.26-3.6 electron units. The applied voltage was 15 kV over a distance of 50 cm producing an average field of 300V/cm. The observed mobilities are in the range: 0.1-0.5 $(cm^2/(kV \cdot sec)$. Evidently, low mobilities are obtained at the high mass values.

As a conservative estimate of release rates, we consider an applied electric field value of 300V/cm, together with the low mobility values quoted above. Hence, we presume ion velocities of order $v_i$=0.03 cm/sec. We examine a gate structure having a pitch distance of 5 microns and a pore diameter of 500 nm. The total pore area within 1 $mm^2$ gate unit will be A(@ 1 $mm^2$ gate)=N·$A_p$ where N is the numbers of pores in 1 $mm^2$ and $A_p$ is the area of a single pore. We get A(@ 1 $mm^2$ gate)=8·$10^{-5}$ $cm^2$. We assume a drug having a density of $\rho$=1 $g/cm^3$. The mass flow through the 1 $mm^2$ gate will be F=$\rho \cdot v_i \cdot$A(@ 1 $mm^2$ gate)=2.4 µg/sec. A single, 500 nm diameter pore, will have a release rate of 60 pg/sec or 0.2 µg/hour.

Note that higher exit velocities are expected when using larger electric fields, or with drugs having smaller mass values. Yet, even the above conservative estimate for flow rate is beyond the required CDRS value. Lower flow rates are easily obtained by increasing pitch length or reducing electric-field values.

We should also take notice that the exit velocity, as derived from the electrophoresis data, is orders of magnitude lower than the speed gained by a free molecule accelerated by a potential difference of 20 mV. A free ion with charge state of one electronic charge unit and having a mass of 200 Daltons will reach speed of 10000 cm/s when accelerated 20 meV. Viscous drag forces and screening effects reduce the ionic velocity to the assumed value of 0.03 cm/s.

Counter flow into the gate of ions having opposite polarity is insignificant. First, this is due to the electric field confinement only inside the gate structure, as evident from FIG. 7. Second, the out-flowing drug molecules will drag opposite polarity ions and neutrals by their high speed relative to the thermal velocities of the body-fluid molecules. We can estimate the thermal velocities of fluid molecules from Stoke's equation of translational diffusion: D=kT/(6·$\pi \cdot$a·$\eta$) (A. Abragam, The Principles of Nuclear Magnetism, Oxford University Press, 1961, p. 301-302). Here D designates thermal drift velocity of a molecule with diameter a. The fluid is at temperature T, k is the Bolzman constant and $\eta$ is the fluid viscosity. Assuming room temperature, fluid with viscosity of water $\eta$=0.01 dyne·sec/$cm^2$ and diameter a=10 nm the translational drift velocity is of order D=2·$10^{-7}$ cm/sec. This is five orders of magnitudes lower than the estimated exit velocities. As a result the fluid molecules will be swept away from the gate by the out flowing drug.

The basic gate structure is extremely versatile. The design details are easily tailored to the specific properties of pharmaceutics and the prescribed therapeutic routine. Gate dimensions and pitch length are freely adjusted in accordance with concrete drug attributes. Different drug release units will differ in these details, yet they benefit from very similar MEMS production tools.

In the MEMS production line, changing matrix-pitch, pore diameter or cell geometry is most easily done by altering the lithographic mask and etching procedure. Different etching protocols are applied corresponding to variations in cone heights and/or insulator thickness. These qualities make it easy to adjust the gate design and the overall CDRS features to a wide spectrum of drugs. Production line is based on identical manufacturing tools, regardless model variations. In summary, harnessing MEMS techniques to the CDRS manufacturing opens opportunities for volume production at reduced cost.

At the device level, in its final form, an operational freedom still exists as regards release-rate or total administered dose. Adaptations are possible by changing electric field values and/or sequence periods. In the modular design, one can also control the number of subunits operating at any given time. By controlling these parameters one can reach release-rates covering many orders of magnitude within a single model. Release parameters can be adjusted on personal basis.

The drug container occupies most of the volume of the present CDRS invention. It is made out of impermeable polymer material or Silicon rubber. If needed, the drug capsule can be coated with another impermeable coating. This will grant bigger freedom in material selection for the container. Various container designs, presently under routine use in other schemes, can be remodeled and integrated with the CDRS. Elastic capsule material is the preferred option. It will automatically collapse when drug content is leveling off. Capsule shape and dimensions are optimized to the specific application. Gate location is arbitrary. It can be chosen to fit available space and preferred site for liberating the pharmaceutical content. Thus, the design versatility offered by the gate properties is enhanced when drug reservoir is integrated with the gate.

The electronic control and command unit is basically a hierarchical system that will be coordinated with the sophistication level of drug administration. Low power CMOS technology is the preferred embodiment. Even at top hierarchical level, electronics specifications are not excessive relative to present day technological know-how. At lower levels of complexity, the electronic system degenerates to mere basic routines, using less elaborate circuitry.

In essence, the electronic command and control unit can be split into two parts: an external, master processing unit, storing the appropriate drug administration routines, and a slave, internal unit supplying bias voltage as command is received from the master unit. Communication vocabulary between master and slave units is fairly limited, simplifying the design of the communication link and associated electronics. The internal unit, encapsulated in a protective coating will occupy a relatively small space out of the total CDRS volume. The electronic unit for simple on/off commands is at the most rudimentary format. It should produce a bias voltage continuously or on command for a certain period. This unit is integrated with the CDRS, without additional external unit. In other, more complex modes, an external command unit is optional. With an external unit the command can be either patient activated or operated autonomically, routine oriented.

The power source can be a miniature, rechargeable battery or capacitor. Power drain due to drug release operation is indeed negligible. Typical bias voltage is of order 10-100 millivolts. The total ionic charge to empty the reservoir is much below 1 C. With these parameters, the energy content of the power source is below 10 mJ. Such a power source is adequate in a continuous drug release mode. No recharging of the battery will be needed even at extended operational period of years.

The electronics and control units, when included, will determine the actual current drain from the power source. These units will consume by far larger power than the gate itself. The power source will need periodic recharging. Recharging implanted power sources is routinely used today in medical practice. Wireless charging option for the embedded battery, or the capacitor will be integrated with the electronic unit. An optional charging scheme is based on the wireless communication link between the external and internal control units.

The drug release device should exhibit high operational reliability. Accordingly, reliability considerations are essential design requisites. We address the issue relying on well proven procedures of enhanced reliability: redundancy of critical elements and design based on series and parallel subunits. Modular construction of the gate coupled to parallel operation of subunits was already mentioned. It will be implemented if necessary. Critical elements, like power source can be split into independent parallel units. In order to eliminate any risk of uncontrolled drug discharge, series operation can be employed. Double gate series design is optional. Another option is through the addition of a fourth, internal electrode having feed holes against the adjacent electrode. The addition of another biased electrode offers another control mode to the gate unit. The extra electrode will guarantee drug discharge only when two independent electrodes are properly biased for gate open condition. Consequently, the failure mode of undesired drug release is reduced to extremely low probability. On the other hand, guaranteed gate-open position is certified by parallel operation of subunits. The addition of third and fourth electrode does not complicate by much the manufacturing process. Also, the volume taken by the extra electrodes is insignificant.

Drug Attributes:

In the electrophoresis process, applied electric-field induces motion of charged molecules. Hence, for drug release applications the pharmaceutics should be either ionic or polar. This is not a very restrictive demand. Presently, most pharmaceutics fall under this category.

Another important quality is drug stability, to guarantee long operational life in a body tissue. Since molecular diffusion of body liquid into the CDRS is hindered by the active gate, we expect drug stability equivalent to shelf storage. Conceivably, in many medical applications we expect years of uninterrupted operation.

Storage volume limitations, combined with the prolonged operational life dictate high drug concentrations, coupled to a release-routine at slow rate. Drug carrier or emulsion need to be chosen in this view. In addition, drug replenishment is optional in some cases, which will further increase the effective life of a device having a small storage volume.

Modes of Operation

Various drug release modes are envisioned. The two basic procedures are low rate, continuous operation, or free-running, pulsed operation at predetermined intervals with fixed-dose rations. Another option is a pulsed mode subject to external or internal command. The external command can be patient controlled.

More demanding processes are possible, when more elaborate electronic units are integrated in the device. The release routine can be pre-programmed in advance or interactive with biofeedback signals. The external command unit will contain most of the hardware and software associated with the device.

Applications

We refer here to a number of applications for the device. This is by no means an exhaustive catalog. The device is a universal platform, enabling controlled release to large spectrum of organic or inorganic molecules.

Regarding medical applications, we address the domain of targeted drug secretion at a specific organ location, where the source of ailment resides. We mainly refer to chronic diseases, uniquely associated with the targeted organ. Among possible ailments we mention: pain management, sever ulcers in gastro organs, urologic problems and many more to this category.

Chemotherapy by locally administered drug combination has also a very promising potentiality.

The device is easily converted to an implantable molecular pump. It is a reversible pump with no moving parts. With one polarity of gate-bias the pump will eject molecules, pulled out from the reservoir. Properly designed, with the inverse gate voltage, it will suck molecules from surrounding environment. In this mode it can be used for internal body screening, at intervals, over long periods of time. The estimated release rate, quoted above, a few micrograms per second from a one millimeter square gate, renders this innovative pump into a powerful tool in the biological and medical fields. Applications in other domains are conceivable.

A related, important list of applications is in the veterinary field. Once again, the main candidates are chronic ailments linked to specific organs.

A multitude of non drug related applications is projected. One example is controlled release of catalysts targeted for regulating chemical reactions. Another use is found in medical screening. The field of molecular biology can benefit from various models of the device. Remote sensing or material tracing are potential applications as well.

What is claimed is:

1. A device for drug release comprising:
   a drug reservoir comprising a gate, wherein opening of said gate releases a drug stored in said drug reservoir;
   an electronic command and control (C & C) unit in communication with said gate that produces a gate bias voltage and time profile supplied to said gate for controlling opening of said gate; and
   a power source for supplying power to said electronic command and control unit, wherein said gate comprises an external electrode formed with at least one exit pore, an internal electrode, an insulating layer that insulates between said external and internal electrodes, and a solid field enhancing member, which is closed to flow therethrough, that extends into said at least one exit pore, and wherein said insulating layer extends along rims of said electrodes, leaving a hollow volume between said electrodes.

2. The device according to claim 1, wherein said insulating layer and said internal and external electrodes are bonded together to form an enclosure impermeable to body fluids.

3. The device according to claim 1, wherein said field enhancing member is a rod.

4. The device according to claim 1, wherein said field enhancing member is a cone.

5. The device according to claim 1, wherein said gate further comprises an additional electrode located below said gate and said internal electrode, and insulated from said gate and said internal electrode by an insulating layer.

6. The device according to claim 1, wherein said at least one exit pore has a diameter from 200 nm to 5 micrometers.

7. The device according to claim 5, wherein said internal electrode and said additional electrode are each formed with at least one feed hole larger in diameter than said at least one exit pore.

8. The device according to claim 7, wherein said at least one feed hole has a diameter of 10-50 microns.

9. The device according to claim 1, wherein said electronic C & C unit comprises a charging element for said power-source and a communication circuit tuned to said external C & C unit.

10. The device according to claim 1, wherein said electronic C & C unit is programmable to provide a delivery routine in accordance with an individual patient response.

11. The device according to claim 1, wherein said gate operates as a reversible pump, wherein a first polarity of said gate bias voltage causes ejection of molecules from said drug reservoir, and a second polarity of said gate bias voltage causes molecules external to said drug reservoir to be sucked into said drug reservoir.

12. The device according to claim 1, wherein said gate bias voltage suppresses molecular flow of fluids into said device.

13. The device according to claim 5, wherein said additional electrode has voltages applied thereto separately relative to said external and internal electrodes.

14. The device according to claim 4, wherein equipotential lines curve around said cone thereby producing electric field enhancement, and no equipotential lines extend outside said gate.

15. The device according to claim 1, wherein said field enhancing member is electrically connected to said internal electrode.

* * * * *